(12) United States Patent
Berry

(10) Patent No.: US 10,293,071 B2
(45) Date of Patent: May 21, 2019

(54) AIR PURIFICATION SYSTEM

(71) Applicant: John Robert Berry, San Diego, CA (US)

(72) Inventor: John Robert Berry, San Diego, CA (US)

(*) Notice: Subject to any disclaimer, the term of this patent is extended or adjusted under 35 U.S.C. 154(b) by 356 days.

(21) Appl. No.: 14/340,912

(22) Filed: Jul. 25, 2014

(65) Prior Publication Data

US 2015/0144803 A1 May 28, 2015

Related U.S. Application Data

(63) Continuation of application No. 13/830,158, filed on Mar. 14, 2013, now abandoned.

(60) Provisional application No. 61/613,776, filed on Mar. 21, 2012.

(51) Int. Cl.
*A61L 9/18* (2006.01)

(52) U.S. Cl.
CPC ...................... *A61L 9/18* (2013.01)

(58) Field of Classification Search
None
See application file for complete search history.

(56) References Cited

U.S. PATENT DOCUMENTS

| | | | | |
|---|---|---|---|---|
| 4,115,280 A * | 9/1978 | Pratt, Jr. | ................... | A23L 3/26 422/186.1 |
| 4,397,823 A * | 8/1983 | Dimpfl | ................... | B01J 19/121 204/157.41 |
| 5,126,020 A * | 6/1992 | Dames | ................... | B01J 19/121 110/237 |
| 5,250,258 A * | 10/1993 | Oh | ................... | A61L 9/18 250/428 |
| 5,323,413 A * | 6/1994 | Gergely | ................... | B01J 19/121 204/157.4 |
| 5,549,735 A * | 8/1996 | Coppom | ................... | B03C 3/155 95/78 |
| 5,589,132 A * | 12/1996 | Zippel | ................... | F24F 3/12 422/24 |
| 5,744,094 A * | 4/1998 | Castberg | ................... | A61L 2/10 250/455.11 |
| 5,770,785 A * | 6/1998 | Tamura | ................... | B01D 53/007 204/157.3 |
| 5,863,752 A * | 1/1999 | Court | ................... | C12M 23/08 422/107 |

(Continued)

*Primary Examiner* — Andrew Smyth
(74) *Attorney, Agent, or Firm* — Knobbe, Martens, Olson & Bear, LLP

(57) ABSTRACT

This invention relates to an air purification apparatuses and methods for air purification. The air purification apparatuses pass air through energy beams that form one or more fields of energy within a chamber to produce an outflow of sterilized air. In some aspects, a charge generation system is implemented to repel particles from the chamber walls. In some aspects, the fields of energy extend across substantially an entirety of the cross sectional area of the interior volume of the chamber and longitudinally within the chamber. In some aspects, a controller is configured to rotate a beam of collimated light energy within the chamber at a rotational velocity corresponding to at least V/W, wherein V is the linear velocity of a particle within the chamber along the longitudinal axis, and W is the width of the beam of collimated light energy.

19 Claims, 11 Drawing Sheets

(56) References Cited

U.S. PATENT DOCUMENTS

| | | | | |
|---|---|---|---|---|
| 6,225,462 B1* | 5/2001 | Berry | C08B 37/0057 | 435/12 |
| 6,673,137 B1* | 1/2004 | Wen | A61L 9/015 | 422/121 |
| 6,730,141 B2* | 5/2004 | Goebel | B03C 3/016 | 422/121 |
| 6,863,864 B1* | 3/2005 | Ingemanson | A61L 2/08 | 219/411 |
| 7,373,254 B2* | 5/2008 | Pierce | A23L 3/26 | 204/157.61 |
| 8,319,195 B2* | 11/2012 | Berry | A61L 9/18 | 204/660 |
| 2004/0017556 A1* | 1/2004 | Nakahara | G03F 1/66 | 355/70 |
| 2004/0228756 A1* | 11/2004 | Berry | A61L 9/18 | 422/22 |
| 2006/0165563 A1* | 7/2006 | Berry | A61L 2/08 | 422/121 |
| 2011/0302881 A1* | 12/2011 | Van Steen | B67C 3/008 | 53/127 |
| 2012/0051977 A1* | 3/2012 | Boodaghians | C02F 1/325 | 422/117 |
| 2012/0074335 A1* | 3/2012 | Berry | A61L 2/08 | 250/455.11 |

* cited by examiner

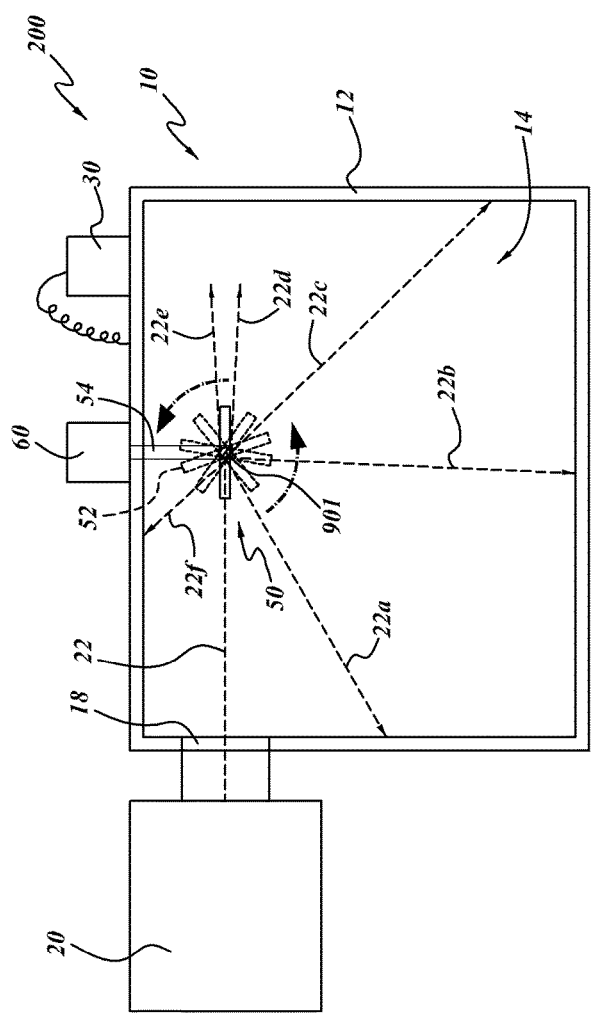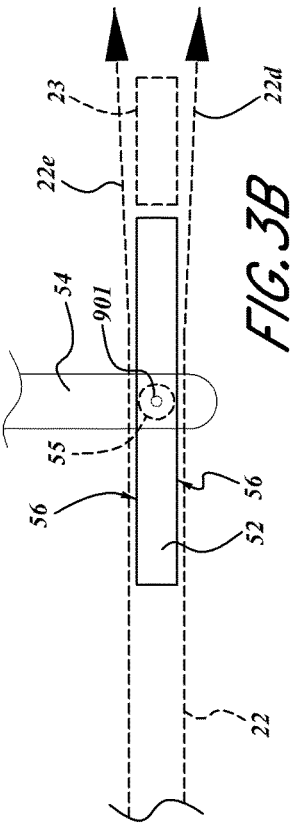
FIG. 3A
FIG. 3B

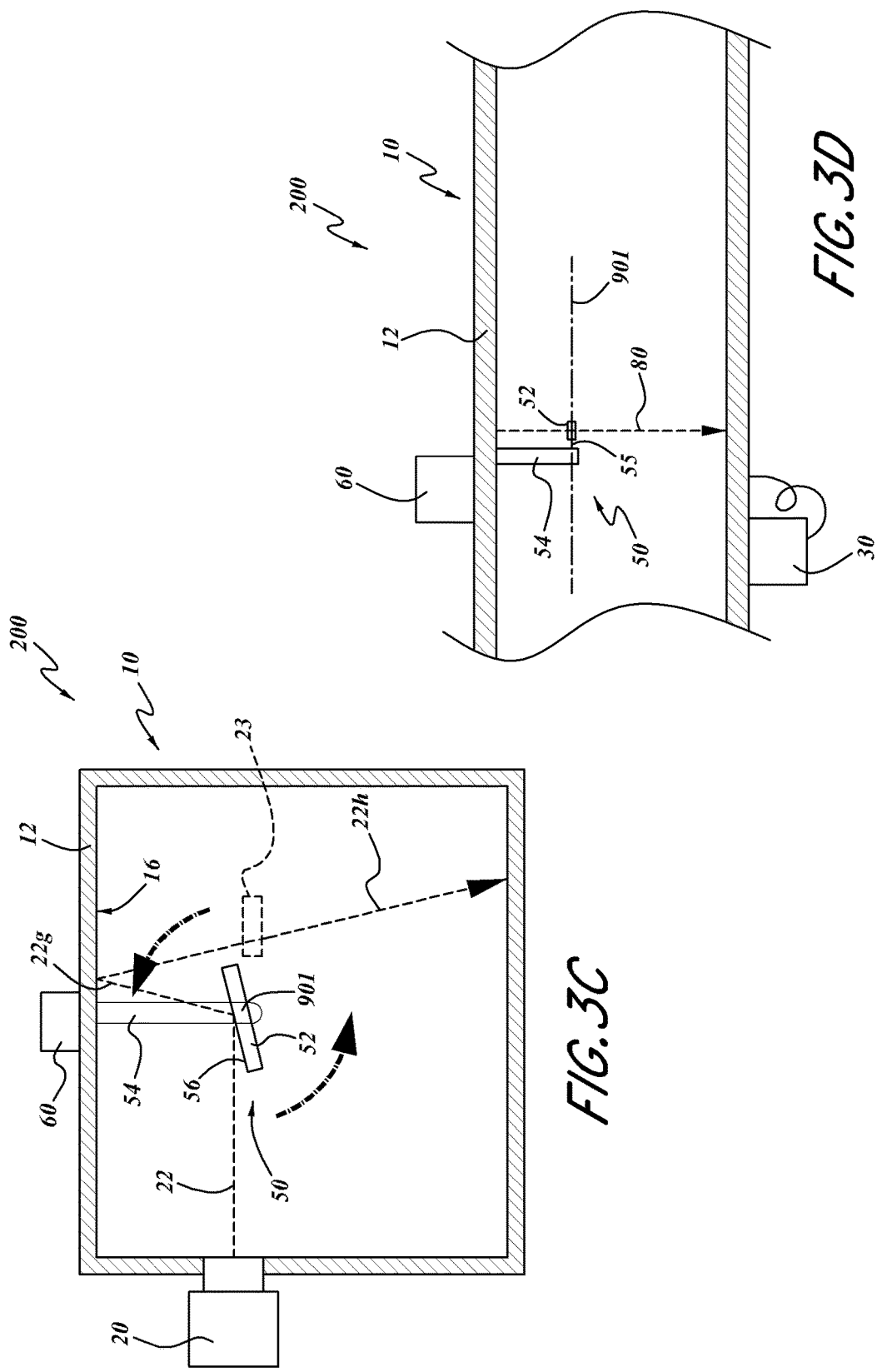

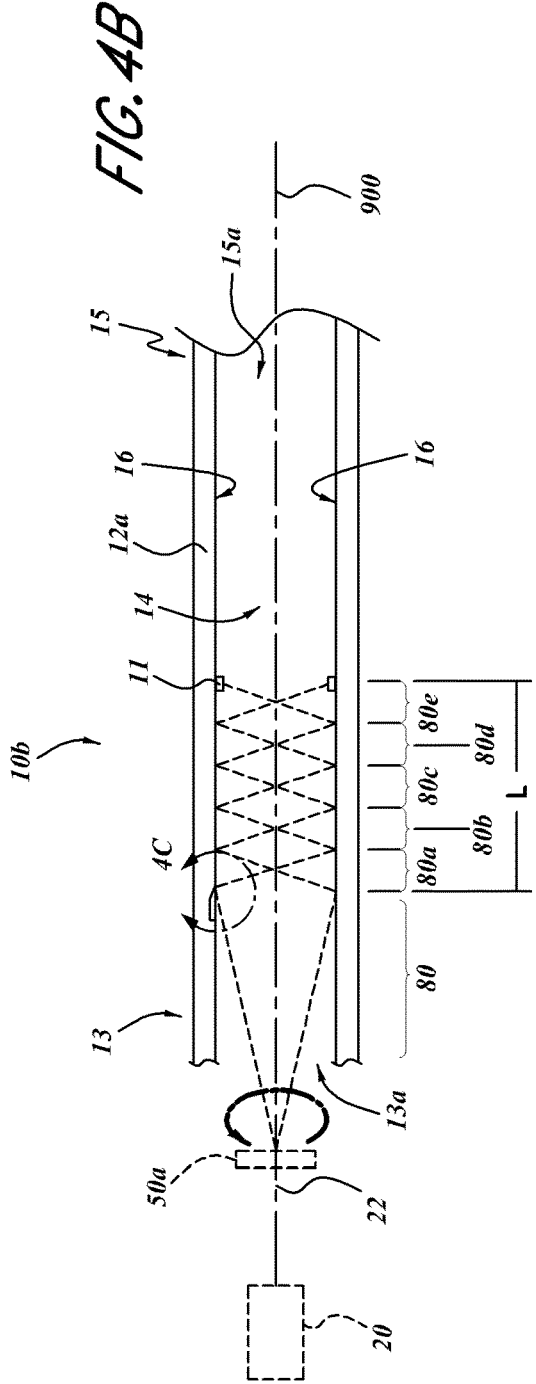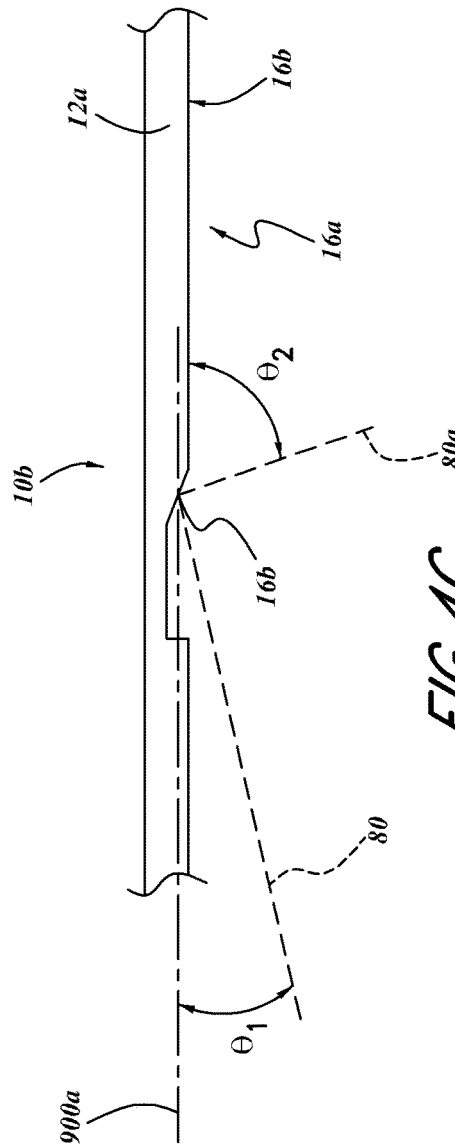

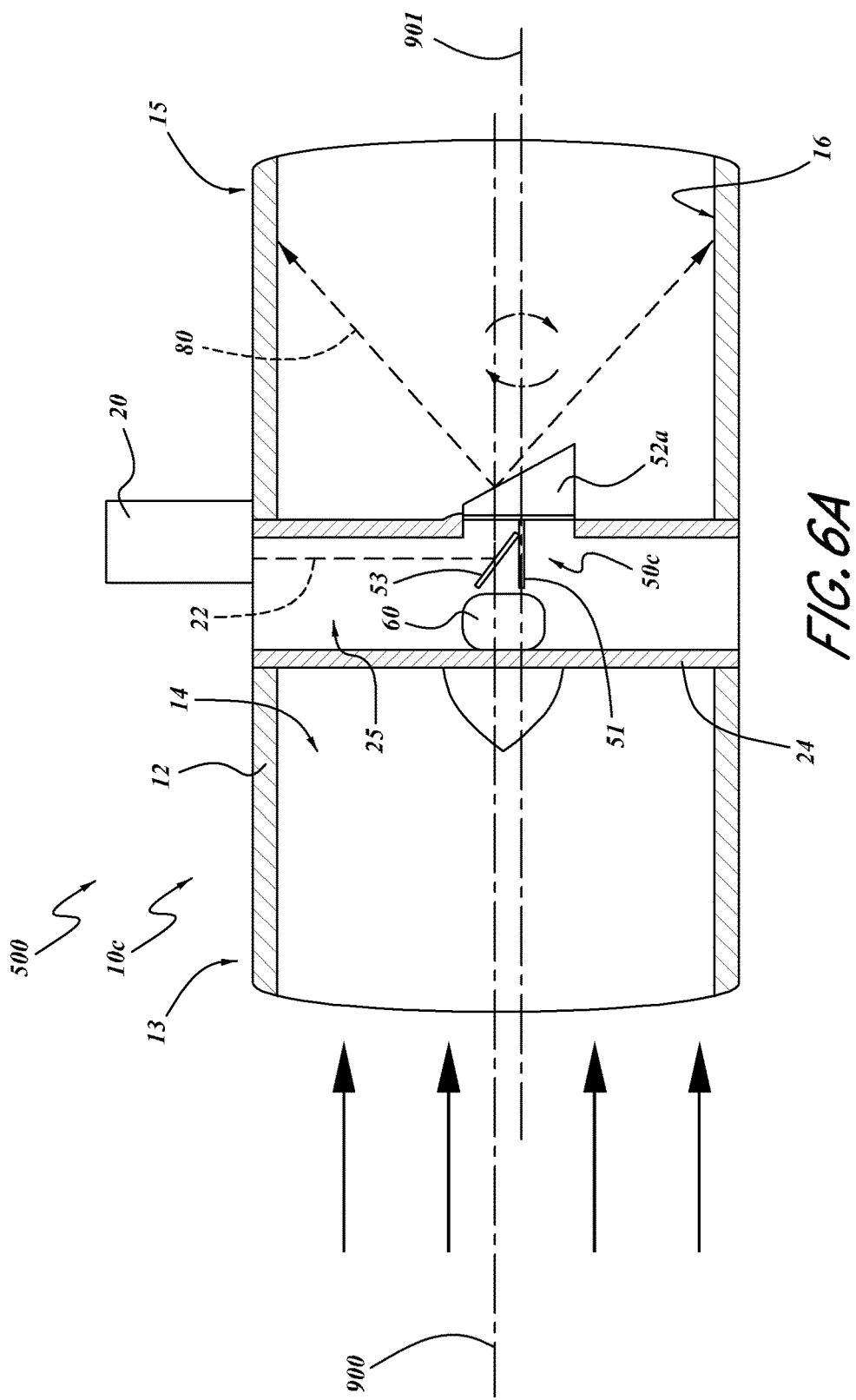

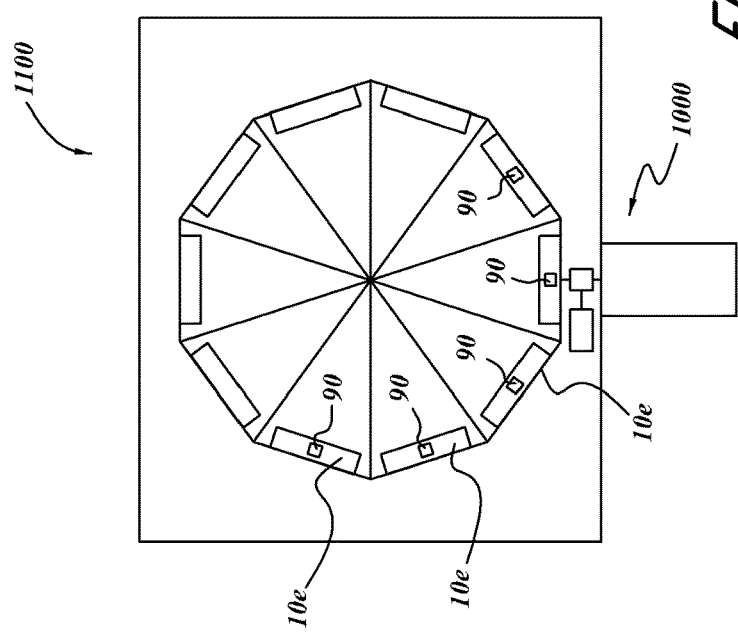
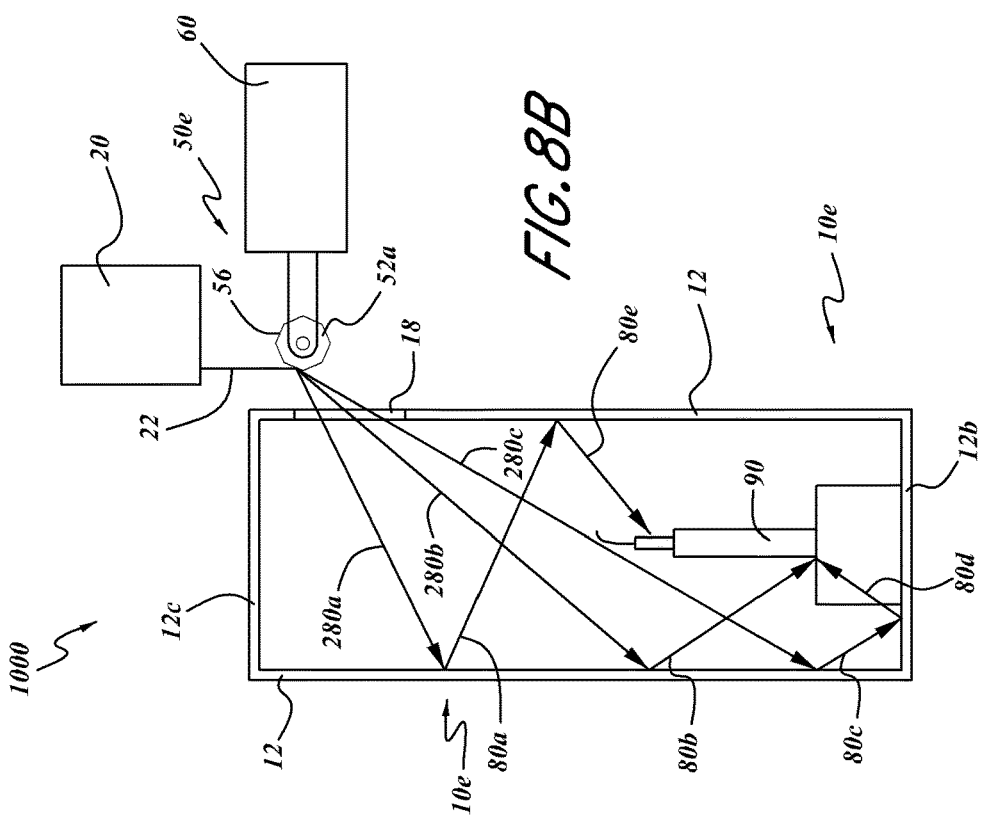

AIR PURIFICATION SYSTEM

CROSS-REFERENCE TO RELATED APPLICATIONS

This application is a continuation of and claims priority to U.S. patent application Ser. No. 13/830,158 filed 14 Mar. 2013, which claims priority to U.S. Provisional Patent Application No. 61/613,776 filed 21 Mar. 2012 under the same title. This application is also related to U.S. patent application Ser. No. 13/249,035 filed 29 Sep. 2011, now issued U.S. Pat. No. 8,319,195, which is a continuation of U.S. patent application Ser. No. 11/302,179 filed 12 Dec. 2005, which is a continuation-in-part application that claims priority benefit of International Application PCT/US2004/018772 filed on 14 Jun. 2004, designating the United States, which claims priority benefits to U.S. Provisional Patent Application No. 60/478,231, filed 12 Jun. 2003 and U.S. patent application Ser. No. 10/640,477 filed 11 Aug. 2003. The entire disclosures of the aforementioned documents are hereby incorporated herein by reference.

BACKGROUND

Field

This application relates generally to an air purification apparatus and methods of air purification.

Description of the Related Art

Air circulation and purification systems are directed to the removal of airborne particulates from the air. Airborne particulates comprise a complex mixture of organic and inorganic substances, bacteria, viruses and any other substances that are small enough to become suspended in the air and atmosphere. Exposure to airborne particulates poses dangers to humans and other organisms because particulates may, for example, induce allergic reactions or cause sickness. The respiratory system is the major route of entry for airborne particulates. The deposition of particulates in different parts of the human respiratory system depends on particle size, shape, density, and individual breathing patterns.

Air circulation systems, for example, air conditioning and heating systems in buildings, aircraft, vessels and vehicles, have been known to circulate airborne viruses and bacteria, which can spread sickness to the occupants. Some air circulation systems in buildings, aircraft, and automobiles use physical filters to trap dust and other particulates. However, physical filters do not to trap small particulates, for example, viruses and spores. Additionally, physical filters can become clogged which in turn decreases air flow, increasing facility costs. Also, the accumulation of particulates on physical filters requires regular cleaning or replacement of the filter, which can interrupt air flow and can be expensive. In some systems, air is purified or sterilized by irradiating the circulating air with ultraviolet lights. One drawback of this method is that dust and particulates collect on the emission source which reduces the intensity of the ultraviolet light. Over time, this collection of particulates reduces the effectiveness of the purification process. Additionally, ultraviolet systems must slow the air to gain more energy to pathogen exposure time to be effective. Slowing the air, as filters also do, significantly increases energy expenses. Therefore, it is desirable to provide a cost effective and efficient means of sterilizing large volumes of air.

The purification of air and objects has been a common requirement for numerous types of practices and environments. For example, sterilized air and objects are required for hospital surgical rooms. The practice of dentistry usually does not require a sterile environment, but it does require the use of sterile dental tools. The state of the art discloses various devices and methods for achieving these objectives. However, the prior art tool sterilization systems may not provide adequate sterilization, or may have similar limitations as those described above generally for air purification systems.

Additionally, recent world developments and increased concern over biological weapons and viruses, such as the SARS virus, or *a. niger* spores, has created a need for simple apparatuses that provide a safe haven by destroying biological pathogens as well as aerosols and suspended particulates. Conventional technology is directed primarily towards filtration methods for removing the above-noted micro objects. However, filtration has its limits described above: efficiency, cost, size, etc.

SUMMARY

The apparatuses, methods and devices of this disclosure each have several innovative aspects, no single one of which is solely responsible for the desirable attributes disclosed herein.

One innovative aspect of the subject matter described in this disclosure can be implemented in an air purification apparatus. The air purification apparatus includes a chamber comprising one or more walls forming an interior volume, wherein at least one of the walls comprises a reflective surface facing inwardly towards the interior volume. The air purification apparatus includes a collimated light source configured to direct a beam of collimated light energy into the chamber. The air purification apparatus includes a charge generation system configured to impart a charge to the one or more walls, to repel particles contained within the interior volume from the one or more walls.

Another innovative aspect of the subject matter described in this disclosure can be implemented in an air purification apparatus. The air purification apparatus includes a chamber comprising one or more sidewalls forming an inner cross-sectional area extended longitudinally along a longitudinal axis to form an interior volume. Each sidewall includes an inwardly-facing reflective surface. The air purification apparatus includes a collimated light source configured to direct a beam of collimated light into the chamber. The air purification apparatus includes a beam redirector disposed within the interior volume and configured to rotate through a complete revolution about a rotational axis such that the beam of collimated light energy is redirected to form a field of collimated light energy extending across substantially an entirety of the cross sectional area of the interior volume and extending longitudinally along the longitudinal axis.

Another innovative aspect of the subject matter described in this disclosure can be implemented in an air purification apparatus. The air purification apparatus includes a chamber. The chamber includes one or more sidewalls forming an interior volume. The one or more sidewalls include one or more surfaces facing inwardly towards the interior volume. The chamber includes a first opening and a second opening configured to allow air to flow through the interior volume from the first opening to the second opening along a longitudinal axis. The air purification apparatus includes a collimated light source configured to direct a beam of collimated light energy into the interior volume of the chamber. The air purification apparatus includes a beam redirector disposed within the interior volume and configured to rotate through a complete revolution about a rotational axis such that the beam of collimated light energy is redirected to form a field of collimated light energy extending across substantially an entirety of a cross sectional area of the interior volume during said revolution. The air purification apparatus includes includes a controller configured to rotate the beam redirector about the rotational axis at a rotational velocity corresponding to at least V/W, wherein V is the linear velocity of a particle within the chamber along the longitudinal axis, and W is the width of the beam of collimated light energy.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

FIG. 3A is a front view of the air sterilization apparatus of FIG. 2.

FIG. 3B is a detailed view of the rotating beam redirector shown in FIG. 3A.

FIG. 3C is another front view of the air sterilization apparatus shown in FIG. 2.

FIG. 3D is a side cross-sectional view of the air sterilization apparatus shown in FIG. 2.

FIG. 4B is a side cross-sectional view of an embodiment of a chamber with a portion of a reflective surface that is oriented to be substantially non-parallel with a longitudinal axis extending through the chamber.

FIG. 4C is a detailed view of the reflective surface shown in FIG. 4B.

FIGS. 6A and 6B are side and front cross-sectional views, respectively, of another embodiment of an air sterilization apparatus configured to form a field of energy extending across an inner cross sectional area of the chamber and longitudinally within the chamber.

FIG. 8B is a side cross-sectional view of another embodiment of an air sterilization apparatus configured to sterilize objects within a chamber.

FIG. 8C is a side cross-sectional view of an embodiment of an air sterilization apparatus that includes a plurality of the sterilization chambers shown in FIG. 8B.

Like reference numbers and designations in the various drawings indicate like elements.

DETAILED DESCRIPTION

Figure 1:
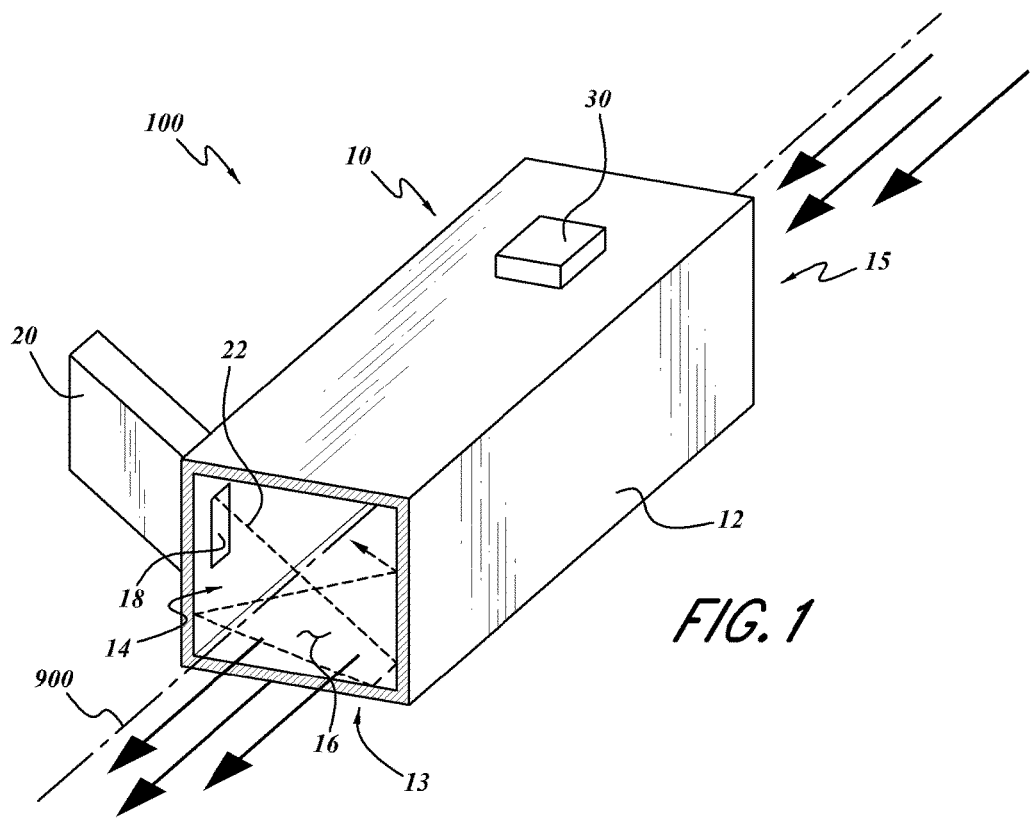
FIG. 1 is a front perspective view of an embodiment of an air sterilization apparatus with a cleaning system.

This application is directed to methods and apparatus for purification of air and objects by directing a beam of energy from an energy source into a chamber. Some embodiments use light energy of proscribed frequencies (wavelengths), energy densities and durations. Some embodiments use a cleaning system that repels particles from a wall of the chamber, to allow the particles to be impacted by the beam of energy, and to keep the reflective surfaces, if any, within the chamber clean. Some embodiments include a beam redirector that rotates an energy beam to form a field of collimated light energy extending across a cross sectional area of an interior volume of the chamber and extending longitudinally within the chamber. Some embodiments include a controller configured to rotate a beam redirector within the chamber at a rotational velocity corresponding to at least V/W, wherein V is the linear velocity of a particle within the chamber, and W is the width of the beam of collimated light energy. Each of these embodiments increase the likelihood of particulate within the chamber being impacted, and thus destroyed, by the beam of energy, or the energy field created by sweeping the beam through the chamber. The duration and frequency of the energy exposure to the particulate depends, in part, upon the residency period of objects within the volume, the intensity and/or energy density of the energy, the frequency or frequencies of the energy, the flow of air through the chamber, and other variables that will be described in more detail below.

Examples of possible particulates suspended in an air flow include bacteria, viruses, toxic gases, toxic molecules, and any other harmful particles. Exposure to a singular energy field within the chamber, or multiple energy fields within the ventilation chamber, destroys and neutralizes spores, bacteria, viruses, protozoa, eukaryotes, other organics, and other particulates. The size of the particulates may vary greatly, however substantially all of the particulates, regardless of their size are irradiated by at least one energy field. In some embodiments, 100% of all the particulates, regardless of size, traveling through the air purification apparatus collide with at least one energy field before exiting the chamber. In other embodiments, 99.8% of all the particulates traveling through the air purification apparatus collide with at least one energy field before exiting the chamber. In yet other embodiments, 99.98% of all the particulates traveling through the air purification apparatus collide with at least one energy field before exiting the chamber. In yet other embodiments, 99.99% of all the particulates traveling through the air purification apparatus collide with at least one energy field before exiting the chamber.

The air purification apparatuses described herein can be integrated into vehicle platforms such as land vehicles, water craft, underwater craft, and aircraft. For example, the system can be configured to be implemented within surface ships and submarines, for example, during a bio attack on a naval fleet. These vehicle platforms are chosen due to their intrinsically controlled internal environment. Using an aircraft platform as an example, the air purification apparatus can be placed preferably downstream of any air conditioning packs that may be present on the aircraft, and close to the external air intake(s). The air purification apparatuses can be located in the central recirculation plenum or at a singular exit from that plenum so all returned air is sterilized. Recirculated air in conventional aircraft systems is only HEPA filtered. The chamber inlet end and outlet end are operative coupled to the main air flow such that all air to be delivered to the interior areas of the aircraft, e.g., cabin and cockpit, may pass through the air purification apparatus. Power for the apparatus can be obtained from the aircraft power harness, taking into account obvious requirements for voltage and load matching. Upon activation of the air purification apparatus, all air being delivered to the interior areas of the aircraft may be subjected to purification. Moreover, if intelligently integrated into the aircraft environmental controls, recirculated air can also be subjected to re-purification thereby addressing issues of contamination originating from within the interior areas of the aircraft. Similar integration approaches can be taken with respect to other vehicle platforms.

In certain embodiments of this series, the air purification apparatus can be portable, e.g., not integrated with or part of a permanent or semi-permanent structure (non-deployable assets). In these embodiments, the apparatus may further comprise an air handler, e.g., a blower having an air displacement element and a motor, and the outlet of the chamber is adapted to fluidly couple with a portable structure such as a container or other transportable rigid structure, or couple with erectable structures such as hazardous materials tents, field medical tents and related medical temporary structures, neonatal care tents, burn recovery tents, and other inflatable tents. Preferably, either type of structure is relatively sealable from an external environment whereby the apparatus provides sterilized air to the interior of the structure and further creates/maintains some level of positive pressure within the structure relative to the environment's atmospheric pressure adjacent to the structure, thus minimizing the undesirable ingress of unconditioned air. The apparatus can be discrete from the structure whereby only a duct or similar air transport conduit is used to operative link the apparatus to the structure, or the apparatus can be integrated with the structure whereby the outlet of the chamber is directly exposed to the interior space of the structure. The optional air handler can be located either upstream or downstream of the apparatus, depending upon design considerations. The air purification systems described herein, such as the portable systems, can be used within the ventilation systems of buildings, vehicles, etc., or can be implemented discretely, for example, to purify a single room or enclosure.

With respect to portable air purification apparatus, it may be desirable to have the apparatus operate off grid. In these embodiments, the apparatus further comprises a power source. The power source may comprise a power generator utilizing an internal or external combustion engine to provide mechanical energy to a suitable electrical generator, the power source may be a battery (rechargeable or not), or the power source may be a fuel cell. For critical applications such as military or first responder environments, fuel cells provide a convenient and reliable means for providing the necessary power to operate even high power lasers and optionally air handlers.

FIG. 1 is a front perspective view of an embodiment of an air sterilization apparatus 100 with a cleaning system 30. Cleaning system 30 can be implemented with any of the air sterilization apparatus described herein. Additionally, "air sterilization apparatus" and "air purification apparatus" are used synonymously herein. Apparatus 100 can include a chamber 10 and a source of energy 20 configured to direct energy into the chamber 10. The energy directed into the chamber 10 can destroy particles within chamber 10, such as stationary particles, or particles flowing through chamber 10.

Chamber 10 can be linear or curvilinear, and/or can have both linear and curvilinear portions. For example, a first end 15 of the chamber 10 can be perpendicular with respect to a second end 13 of the chamber 10. The degree of curvature of the chamber 10, and the angle between first end 15 and second end 13 may cover any possible range. For example, the end 15 to the chamber 10 can be oriented approximately 45 degrees from the second end 13 of the ventilation duct.

The chamber 10 can comprise one or more sidewalls 12 that form an interior volume 14. In some embodiments, sidewalls 12 can comprise a sheet metal or other thin material, similar to the ductwork within a ventilation system. However, it will be understood that sidewalls 12 can comprise any structure that forms the interior volume 14. For example, sidewalls 12 can comprise a portion of a housing, manifold, block, or other structure. For example, sidewalls 12 can comprise a portion of a larger support structure in or on which the other components of chamber 10 are supported or contained.

The interior volume 14 of chamber 10 can have various cross-sectional shapes, such as the square-shape shown, to form a square duct. The interior volume 14 can have a round cross-sectional shape, to form a cylindrical duct, or any other regular or irregular cross-sectional shape suitable to form an interior volume when extended longitudinally along a longitudinal axis 900. It will be understood that longitudinal axis 900 follows the general shape of interior volume 14, and is not necessarily straight. For example, the chamber 10 can form a curvilinear duct, in which the longitudinal axis 900 follows the same curvilinear shape longitudinally within the duct. Generally, the ends 13, 15 can include openings 13A, 15A, configured to attach to a ventilation system and allow air to flow through the interior volume 14 along the longitudinal axis 900, such that chamber 10 forms a portion of a ventilation duct. However, in some embodiments, the chamber 10 can be a substantially closed chamber, wherein ends 13, 15 include additional sidewalls to cover openings 13A, 15A. For example, chamber 10 can be configured to be used as a sterilization apparatus for medical equipment.

The energy source 20 can comprise a collimated light source, such as a laser or other source of non-ionizing collimated electromagnetic radiation capable of directing a beam of collimated light energy 22 towards a target volume, and irradiating the volume. The energy source 20 can comprise any other type of energy source capable of directing a beam of energy into a volume, having a power output sufficient for achieving the intended purpose of the apparatus and methods. Energy source 20 can provide a beam of sufficient strength to destroy or neutralize one or more of dust particles, pollen, pathogens, allergens, gasses, or other particulates that are present in the flow of air through the system. The energy source 20 may be of the continuous wave or pulsed type, with many embodiments employing a pulsed type for reasons well known to those skilled in the art. Depending upon the energy density for a given application, a 10 watt $CO_2$ laser emitting radiation in the infrared region may be sufficient and higher power and/or additional lasers may be employed. In some embodiments a 15 watt laser is used, and in still other embodiments a 60 watt laser is used. In an embodiment, the wavelength of the laser or energy of the emitted beam(s) is selected based upon the target species identified for neutralization. For example, in some embodiments a wavelength ranging between approximately 1056 and 1064 microns (μm) provided benefits in neutralizing certain species, such as spores of *Aspergillus niger*.

The energy source 20 can be positioned outside the chamber 10, and the beam 22 can be directed through one or more openings 18 extending through sidewall 12. The opening 18 can include a transparent optical window or other structure to prevent contamination into chamber 10 through opening 18. The optical window may or may not be used to redirect at least on beam through sidewall 12. The optical window may be placed along any portion of the chamber 10. One having skill in the art may vary the placement of the optical window to optimize exposure of the energy field to the inside of the chamber 10.

The optical window may be constructed out of any suitable material known to those having skill in the art. In an embodiment, the optical window comprises a material that allows at least one beam 22 of energy to pass from the outside of the chamber 10 to the inside of the chamber 10. In another embodiment, the optical window comprises a material that allows for substantially all of the collimated light energy to pass through the outside of the optical window and into the chamber.

At least one of sidewalls 12 can include a reflective surface 16, to reflect the beam 22 within chamber 10. In some embodiments, each of sidewalls 12 includes a reflective surface 16, to repeatedly reflect and redirect the beam 22 within chamber 10. Other embodiments described herein provide additional ways to further reflect and redirect the beam 22 within chamber 10.

Surface 16 may be curvilinear, rectilinear or any combination thereof. Furthermore, a portion or the entire interior surface 16 may have various characteristics including highly reflective properties, surface undulations (linear or curvilinear) or features to assist in beam scattering or intended beam redirection. Moreover, the interior surface may be rigid or flexible. If flexible, the surface may be acted upon by a force (mechanical, electrical or pneumatic) to cause deflection thereof. In certain embodiments, the deflection is cyclical and characterized as a vibration.

The reflective surface 16 can be any layer, coating, or other structure suitable to reflect an energy beam such as a collimated light source. For example, the reflective surface 16 can comprise a reflective metal, such as gold, aluminum, silver, or nickel, reflective polymers, or other suitably reflective materials. The one or more reflective inner walls of the chamber 10 can reflect the beam 22 so that air passing through the chamber 10 passes through multiple beams or fields of energy. One having skill in the art may increase or decrease the length of the chamber 10 to increase or decrease the number of fields or beams through which air must pass before exiting the chamber 10.

Cleaning system 30 can be configured to repel particles contained within the inner volume 14 from the sidewalls 12, to prevent particles from settling on and accumulating on sidewalls 12. Particles that settle on sidewalls 12 may provide a focal point for beam 22 on reflective surface 16, causing overheating and decreasing the reflective functionality of surface 16. In some situations, particle accumulation on sidewall 12 may cause beam 22 to burn a hole through sidewall 12, causing system contamination. To repel particles from the sidewalls 12, cleaning system 30 can comprise a charge generation system configured to impart a charge on one or more of sidewalls 12, for example, to surface 16. The charge can be provided at a similar polarity as the particles within chamber 10. For example, it has been observed that particles flowing within a ventilation system may naturally form a charge, such as a negative charge. Thus, charge generation system 30 can employ a similar charge to sidewalls 12 as the particles, such as a negative charge, to repel the particles as described. In some embodiments, a charge generation system can be employed to actively charge the particles, in addition to the aforementioned natural charge that may be formed. For example, a screen, nodes, or other structure can be extended across or from the interior of chamber 10, and the screen or nodes can be charged with another charge generation system, to impart the same charge to particles passing through the screen or node field, prior to contacting and being destroyed by beam 22. Such active charge to the particles can further prevent particle accumulation on sidewalls 12 when sidewalls 12 are similarly charged by charge generation system 30. Charge generation system 30 can comprise any suitable power source, such as battery, electrode, or other related electronic components, capable of placing a charge on sidewalls 12. Cleaning system 30 is very different from conventional ventilation cleaning systems, in which the goal was to attract particles to a device mounted on a sidewall, such as a filter or adhesive, etc., rather than repelling them, and allowing them to continue to flow within the ductwork being decontaminated. The sidewall charge may be provided by redirected waste thermal energy formed within apparatus 100, or within a system within which apparatus 100 is implemented.

FIG. 2 is a front perspective view of an embodiment of an air sterilization apparatus 200 with a rotating beam redirector 50. FIG. 3A is a front view of the air sterilization apparatus 200 of FIG. 2. FIG. 3B is a detailed view of the rotating beam redirector 200 shown in FIG. 3A. FIG. 3C is another front view of the air sterilization apparatus 200 shown in FIG. 2. FIG. 3D is a side cross-sectional view of the air sterilization apparatus 200 shown in FIG. 2.

Referring to FIGS. 2-3D, beam redirector 50 can comprise an optical element 52 configured to rotate about a rotating axis 901. The optical element 52 can rotate through a complete revolution about the axis 901, and in some embodiments, through multiple complete revolutions. Such rotation can be provided, for example, through a motor 60, a motor shaft 54, and an optical element shaft 55. Any other structure suitable to impart rotational motion on beam redirector 50 about axis 901 can be implemented, such as other rotational actuators and the like. Optical element 52 can comprise any suitable structure configured to redirect the beam 22 within volume 14 of chamber 10, such as one or more suitably reflective (e.g., planar) surfaces 56. In some embodiments, optical element 52 can comprise other reflective, refractive, transmissive, or other structures, that can redirect a beam of light energy. In some embodiments, optical element 52 can redirect a beam of light energy by dispersing (e.g., bisecting) a single beam, such as a laser beam, into two or more beams. In some embodiments, optical element 52 can change the direction of a beam of light energy by changing the wave velocity of the beam.

The rotation of optical element 52 can allow beam 22 to be redirected at various incident angles within chamber 10, as illustrated schematically by the beams 22A-22F in FIG. 3A. Through said rotation, optical element 52 can reflect and sweep beam 22 around the inner perimeter of chamber 10, and form a field of energy 80 (FIG. 3D) that extends across the cross sectional area of the interior volume 14. The energy field 80 will increase the likelihood of contact between particulate matter traveling through chamber 10 and the energy within chamber 10 provided by energy source 20, thus increasing the sterilization effects within chamber. The field 80 can extend at an angle that is substantially orthogonal relative to the axis 900, or can be at an angle thereto. In some embodiments, the field 80 can comprise an approximately two-dimensional shape, for example, when the beams 22A-22F, and the other reflective beams forming the field 80, are co-planar. The embodiments of apparatus 200 shown in FIGS. 2-3D can produce a field of energy 80 that is approximately two-dimensional. Alternatively, the field can comprise a three-dimensional shape, when it comprises a plurality of reflective beams that also extend longitudinally along axis 900, as described further below.

In use, air enters the chamber 10 through the opening 13A, and passes through energy field 80. As the air passes through energy field 80, any particles suspended in the air, are irradiated. Energy field 80 is generally of sufficient strength to neutralize the particulates. Once the air exits the chamber 10 through the opening 15A, the air is substantially sterile.

Referring to FIG. 3B, a vortex 23 can be formed within a portion of volume 14 in which the field of energy 80 formed by the reflected and rotated beam 22 may not reach. For example, vortex 23 can be formed within portions of volume 14 that are positioned behind optical element 52 relative to the collimated light source 20. Thus, particles longitudinally moving through chamber 10 may not be contacted within vortex 23 by beam 22, and thus, may not be destroyed, by beam 22. The width shown of beam 22 in FIG. 3B is for illustrative purposes only, and to demonstrate how vortex 23 can be formed.

Referring to FIG. 3C, to increase the likelihood of contact between a reflection of beam 22 and a particulate within vortex 23, at least one sidewall 12 of chamber 10 can include the reflective surface 16. In such an embodiment, beam 22 can initially be redirected by beam redirector 50 towards surface 16, as depicted by beam 22G, and then reflected on the sidewall surface 16, to form beam 22H. Beam 22H can cross vortex 23, and thus can increase the likelihood of contact between beam 22 and particulate within vortex 23. As such, a field of energy 80 can extend across substantially an entirety of the cross sectional area of the interior volume 14, and contact (and destroy) an increased percentage of particles passing therethrough. Vortex 23 can be crossed and impacted by the energy beam when the field of energy is reflected longitudinally down the chamber, as described further herein, and shown in the embodiments of FIGS. 4A-7B.

Referring again to FIG. 2, a controller 70 can be employed to control various parameters of the energy source 20, motor 60 (or other rotational device), and cleaning system 30. Controller 70 may control the polarity, frequency, amplitude, or other parameters of the charge imparted by cleaning system 30 to portions of the chamber 10. Controller 70 can control the flow velocity of the air through the chamber 10, through control of air flow devices, such as fans, pumps, valves, or other devices. Controller 70 may control various characteristics of the energy source 20, such as the amplitude, frequency, wavelength, width (e.g., diameter), or other characteristics. Controller 70 may pulse or otherwise vary when beam 22 is emitted from the energy source 20. For example, to prevent errant reflection, controller 70 may interfaces with energy source 20 to switch it on and off in synchronicity with the operation of beam redirector 50. Controller 70 can comprise a personal computer, or any other hardware, firmware, software, and the like suitable to control a system such as apparatus 100.

In some embodiments, controller 70 may control the speed of the rotation of the beam redirector 50. For example, controller 70 may control the speed of rotation of the beam redirector 50 based upon the linear speed of a particle within the chamber 10, and the width of the beam 22, to increase the likelihood that the beam 22 would contact (e.g., destroy) the particle within the field of energy created during a single rotation of the beam redirector. As such, controller 70 can be configured to rotate configured to rotate the beam redirector 50 about the rotational axis 901 at a rotational velocity ω corresponding to V/W, wherein V is the linear velocity of a particle within the chamber along the longitudinal axis 900, and W is the width (e.g., diameter) of the beam of collimated light energy. Examples 1 and 2 below provide further details on this relationship and method of controlling beam redirector 50 with controller 70. Controller 70 can be employed within any of the air purification apparatuses described herein.

Figure 4A:
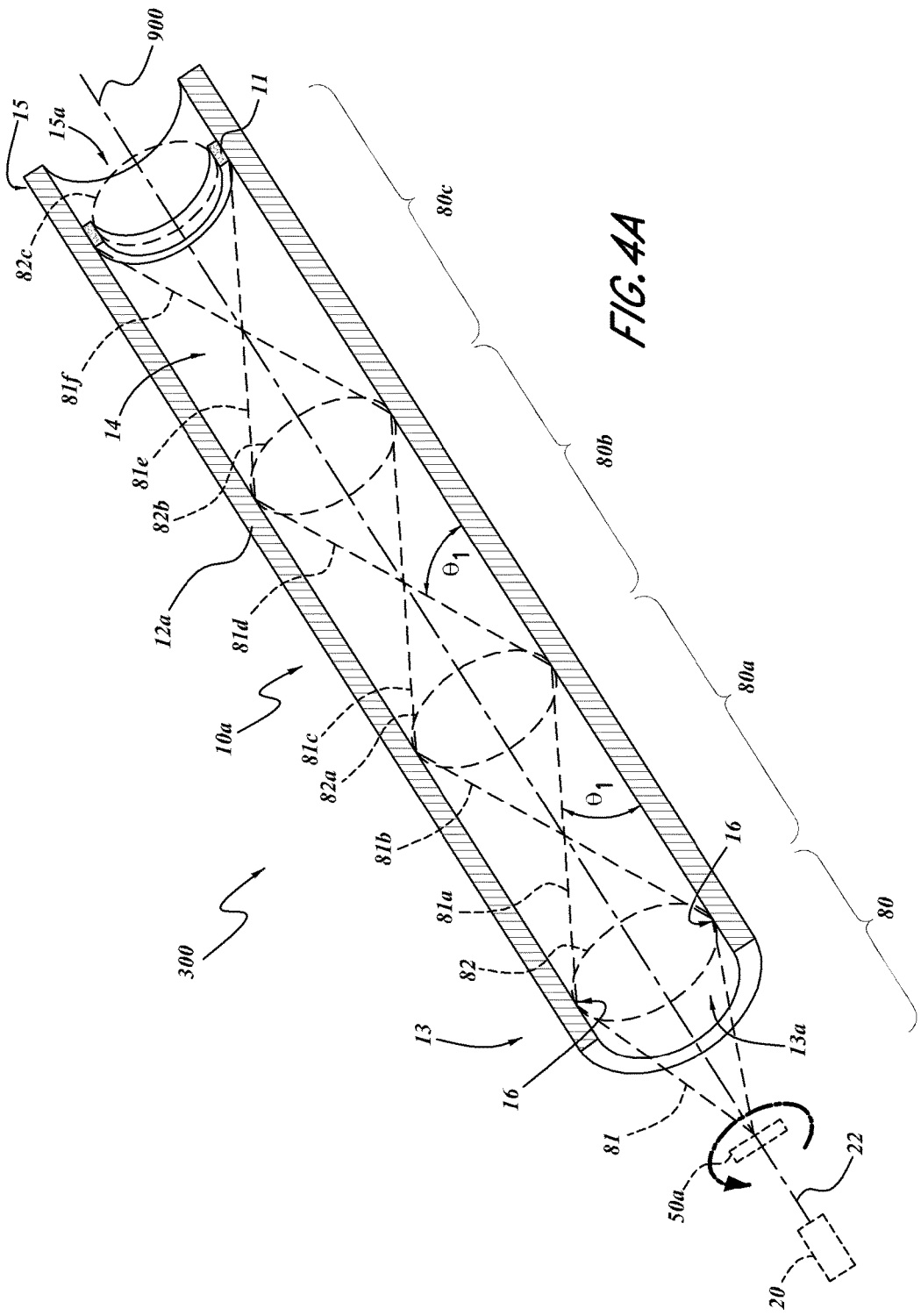
FIG. 4A is a side perspective cross-sectional view of an embodiment of a chamber with a field of collimated light energy extending across an inner cross sectional area of the chamber and longitudinally within the chamber.

FIG. 4A is a side perspective cross-sectional view of another embodiment of an air sterilization apparatus 300 with a field of energy 80 extending across an inner cross sectional area of a chamber 10A and longitudinally within the chamber 10A.

Chamber 10A can be similar to chamber 10 in FIGS. 1-3D, and is shown with a cylindrical sidewall 12A for illustrative purposes only; chamber 10A and sidewall 12A can comprise other shapes. Sidewall 12A can include the reflective surface 16. A laser 20 and beam redirector 50A are shown schematically; beam redirector 50A can be similar to beam redirector 50 or the other beam redirectors described herein. Beam redirector 50A can be configured to redirect beam 22 from laser 20 to form an energy field 80. Energy field 80 can be similar to that formed by beam redirector 50 and redirected beams 22A-22H in FIGS. 2-3D. In this embodiment, the beam redirector 50A can be configured to direct beam 22 both radially outwardly and longitudinally with respect to axis 900, such that energy field 80 is a three dimensional energy field. For example, energy field 80 can comprise a first portion 81 that extends both radially outwardly and longitudinally with respect to axis 900, until forming a second portion 82 that contacts and forms a perimeter along an inner surface of sidewall 12A. A three-dimensional energy field with a controlled shape such as energy field 80 can increase the likelihood that any particulate traveling through volume 14 will be contacted by a portion of the energy beam 20 that forms field 80. The three-dimensional energy field can comprise a number of different shapes, depending on the configuration of the chamber, its sidewalls, and the beam director. In the illustrated embodiment, energy field 80 is approximately frustro-conically shaped.

In embodiments with reflective surface 16, energy field 80 can then be reflected off reflective surface 16 and repeated, radially and longitudinally along axis 900 down the interior volume 14 of chamber 10A, to form one or more additional reflected energy fields 80A, 80B, 80C. The reflective angle of the beams impacting and reflecting from surface 16 are shown as angle $\theta_1$. Such repeated, reflected, three-dimensional energy fields further increase the likelihood that any particulate traveling through volume 14 will be contacted by a portion of the energy beam 20 that forms fields 80A, 80B, 80C, etc. Additionally, any particulate that is not destroyed through an initial contact with energy field 80, will have an increased likelihood of subsequently being destroyed by one of the subsequent, reflected energy fields. In some embodiments, the length of the chamber is adjusted so that air flowing through the chamber passes through five different fields of light energy before exiting the chamber. In another embodiment, the length of the chamber is adjusted so that air flowing through the chamber passes through four different fields of light energy before exiting the chamber. In another embodiment, the length of the chamber is adjusted so that air flowing through the chamber passes through three different fields of light energy before exiting the chamber. In another embodiment, the length of the chamber is adjusted so that air flowing through the chamber passes through two different fields of light energy before exiting the chamber. In another embodiments, as many as 19 different fields of light energy can be reflected within the chamber, and more or less fields are within the scope of the invention.

Embodiments of the air ventilation systems described herein can include an energy abatement device positioned within the chamber to limit the travel of the energy beams or fields produced by the energy source within the chamber. For example, the energy abatement device can prevent a portion of the energy field from exiting the chamber of the air ventilation system and traveling within the ventilation system to which the chamber is attached. Any suitable material known to one having skill in the art as being capable of absorbing beam energy may be used for the energy abatement device, and/or the energy abatement device may be located along any portion of an interior of the chamber.

An example of an energy abatement device 11 is illustrated in FIG. 4A. Energy abatement device 11 can form an annular ring-like shape that extends around an inner perimeter or circumference of sidewall 12A. Other shapes can be used, depending on the shape of the chamber. One or more energy abatement devices can be employed, and the devices can be positioned at various locations within the chamber. For example, one or more energy abatement devices can be located at or near either or both of ends 13, 15. In some embodiments, the energy abatement device can be fitted with one or more heat sinks. Any suitable heat sink known to those having skill in the art may be used. The heat sink may be further connected to device that further dissipates or redirects the heat energy absorbed by the heat sink. It will be understood that energy abatement device 11, or other suitable devices, can be employed within any of the chambers and air purification apparatuses described herein.

In some embodiments, one or more light baffles can be extended across the inner volume of the chambers described herein. The baffles can permit air flow thereby but occlude any direct or indirect beam from exiting the chamber. The baffles can be constructed from any suitable material that absorbs and/or reflects beam energy. If the baffles absorb the energy, it may also be desirable to include means for cooling the baffles if the air flow rate is insufficient for the task. Examples of embodiments of light baffles that can be implemented within the air purification apparatuses described herein are disclosed in U.S. Pat. No. 8,319,195, entitled "Methods and Apparatus for Sterilization of Air and Objects" and issued Nov. 27, 2012, the entire contents of which are incorporated herein by reference.

In some embodiments of the air purification apparatuses described herein, a safety mechanism can be employed to disable energy source 20, and prevent injury, such as retina damage to a person. For example, a shock (e.g., earthquake) sensor can be connected to energy source 20 (or its related controller) that deactivates energy source 20 in the event that it is subjected to shock above a threshold. A secure light box or similar device can be employed to prevent tampering with the airflow apparatuses described herein, and accidental exposure to energy emitted from energy source 20.

FIG. 4B is a side cross-sectional view of an embodiment of a chamber 10B with a portion of the reflective surface that is oriented to be substantially non-parallel with a longitudinal axis extending through the chamber 10B. FIG. 4C is a detailed view of the reflective surface shown in FIG. 4B.

Referring to FIG. 4C, the reflective surface 16 can include a first portion 16A that extends generally along and parallel with a longitudinal axis 900A. The longitudinal axis 900A extends approximately longitudinally within chamber 10B, similar to axis 900 (FIG. 4B), but is shown radially offset from the center of volume 14.

The reflective surface 16 can include a second portion 16B oriented to be substantially non-parallel with the longitudinal axis 900A. The depth, width, angle, or number of reflective portions 16B may be adjusted to redirect the path of the fields of energy 80 within chamber 10B. For example, portion 16B can allow the entry angle $\theta_1$ of energy field 80, defined as the angle between energy field 80 and axis 900A, can be less than the exit angle $\theta_2$ of energy field 80, defined as the angle between the reflected energy field 80A and axis 900A. Such reduction between angle $\theta_1$ and $\theta_2$ can decrease the total length L consumed by the repeated, reflected energy fields within chamber 10B, and thus decreasing the size of air sterilization apparatus within which chamber 10B is implemented.

The second portion 16B can have any of a number of different configurations. For example, the second portion 16B can extend around some, or substantially the entirety of an inner perimeter of chamber 10B. Second portion 16B can protrude from, or can be recessed with respect to first portion 16A of reflective surface 16. A recessed portion 16B can reduce flow restrictions within chamber 10B. In some embodiments, second portion 16B comprises a groove that is recessed within reflective surface 16. It will be understood that the second portion 16B can be implemented within other chambers and other air purification apparatuses described herein.

In some embodiments, both the length of the chamber and the depth, width, and number of angled reflective portions are configured so that air passing through the ventilation chamber must pass through at least five, four, three, or two fields of energy before exiting the ventilation chamber.

It will be understood that both the two and three dimensional energy fields described herein can be formed within various shapes and sizes of chambers, at various orientations within the chambers, and can be formed with various embodiments of beam redirectors. Additional embodiments of air sterilization apparatus that can form energy fields are shown in FIGS. 5A-10C.

Figure 2:
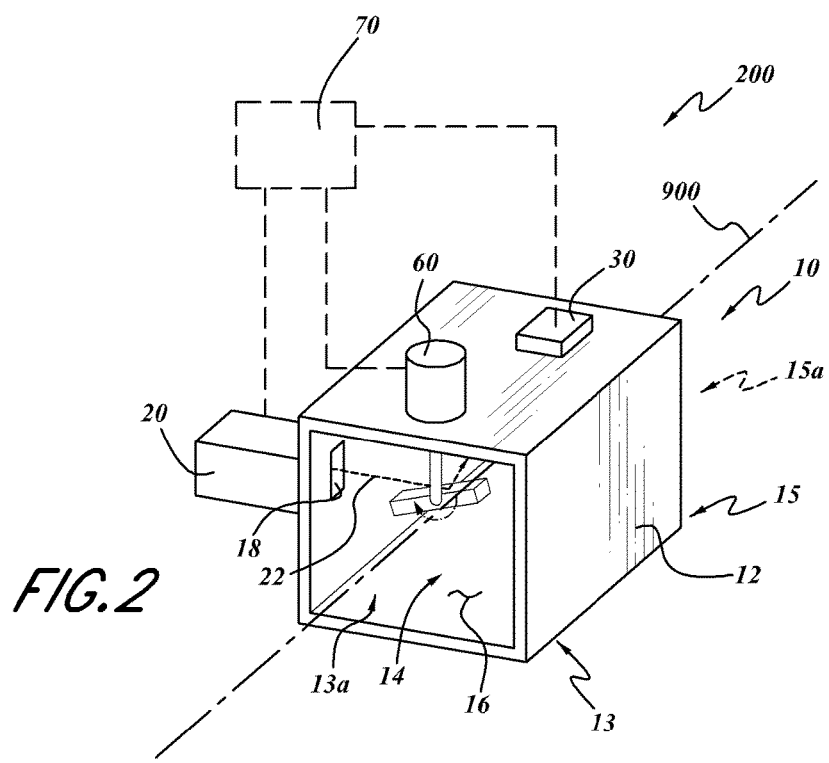
FIG. 2 is a front perspective view of an embodiment of an air sterilization apparatus with a rotating beam redirector.
Figures 5A, 5B:
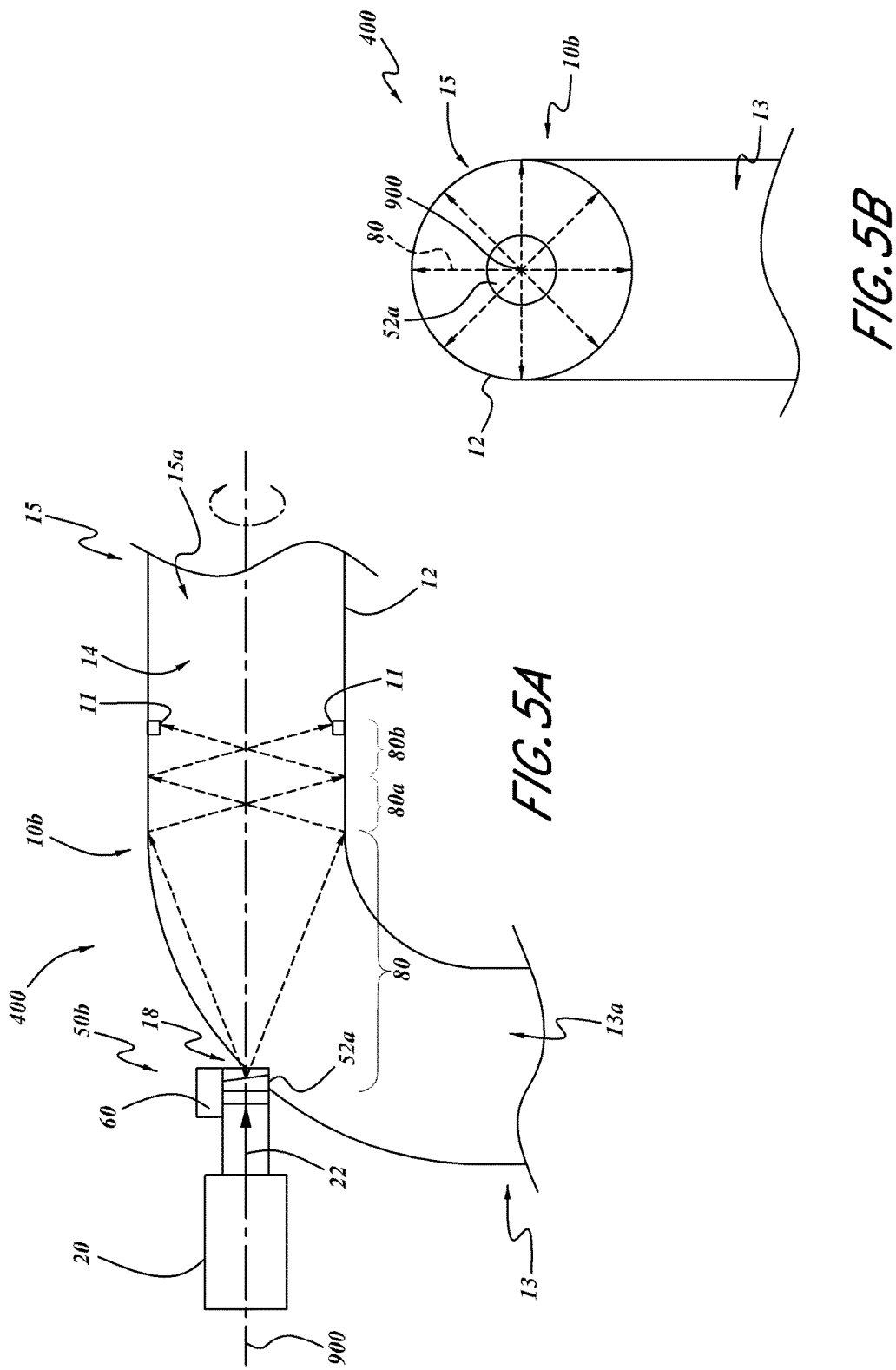
FIGS. 5A and 5B are side and front views, respectively, of an embodiment of an air sterilization apparatus configured to form a field of energy extending across an inner cross sectional area of the chamber and longitudinally within the chamber.

FIGS. 5A and 5B are side and front views, respectively, of an embodiment of an air sterilization apparatus 400 configured to form a three-dimensional field of energy 80 extending across an inner cross sectional area of a chamber 10B and longitudinally within the chamber 10B. Apparatus 400 comprises a beam redirector 50B configured to form energy field 80 within chamber 10B. Beam redirector 50B can comprise an optical element 52A configured to rotate about an axis, similar to optical element 52 in FIGS. 2-3D. Element 52A can rotate about a rotating axis that is approximately collinear with axis 900, or offset from axis 900. Optical element 52A can be configured to redirect beam 22 from energy source 20 similar to, and can be similarly configured as optical element 52 (FIGS. 2-3D). In some embodiments, optical element 52A can implement a lens that redirects the beam 22 through refraction instead of or in addition to reflection. The resulting shape of field 80 can be similar as those other embodiments described herein. Ends 13 and 15 of chamber 10B can be oriented at an angle with respect to each other, such that chamber 10B forms an elbow. Beam redirector 50B can positioned within the elbow, and can be positioned internally within chamber 10B (within volume 14) or externally to chamber 10B.

Figure 6B:
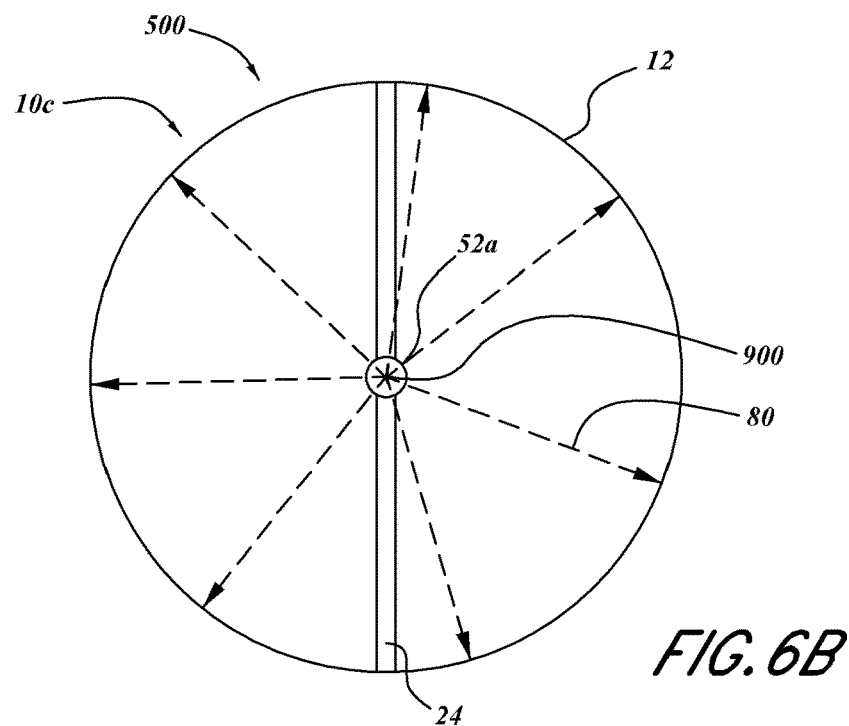

FIGS. 6A and 6B are side and front cross-sectional views, respectively, of another embodiment of an air sterilization apparatus 500 configured to form a three-dimensional field of energy 80 extending across an inner cross sectional area of a chamber 10C and longitudinally within the chamber 10C. Apparatus 500 can include a beam redirector 50C and refractive optical element 52A, similar to beam redirector 50B and optical element 52A shown in FIGS. 5A and 5B. In this embodiment, the beam redirector 50C can be mounted within volume 14, and can be positioned within bent portion of chamber 10C, such as an elbow, or within a substantially straight portion of chamber 10C. A support member 24 can extend from sidewall 12 into chamber volume 14 to provide support to beam redirector 50C. Support member 24 can include an inner channel 25 through which the energy beam 22 can be directed from energy source 20. The energy beam 22 can be directed through optical element 52A by directing beam 22 in a first direction (e.g., downwardly as shown) from energy source 20, and then reflected off a reflective element 53 in a second direction (e.g., horizontally as shown) through optical element 52A. Optical element 52A can be rotated about rotational axis 901 to form energy field 80. Optical element 52A can be rotated by a motor 60 and driveshaft 51 mounted on support member 24, or through other suitable rotational devices and components. Support member 24 can extend from a single side 12 of chamber 10C, or can extend from a first side to a second side, to provide additional support and stability to components mounted thereon. An aerodynamic element 26 can be provided on a portion or all of the upstream and/or downstream side of support member 24, to reduce the drag on the air being ventilated through chamber 10C.

Figure 7A:
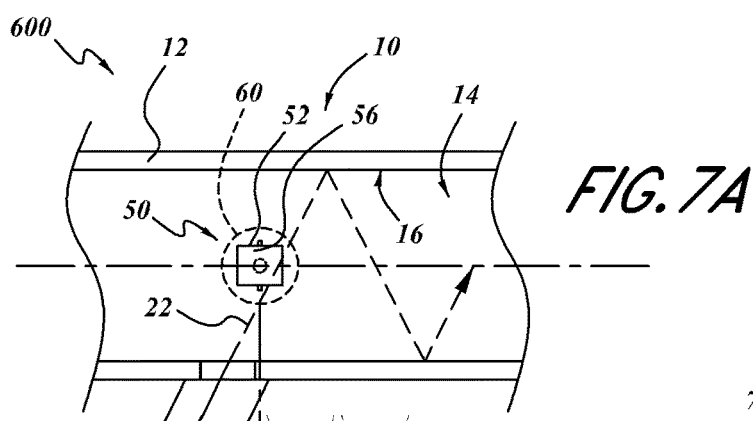
FIGS. 7A and 7B are top cross-sectional views of other embodiments of an air sterilization apparatus configured to form a field of energy extending across an inner cross sectional area of the chamber and longitudinally within the chamber.
Figure 7B:
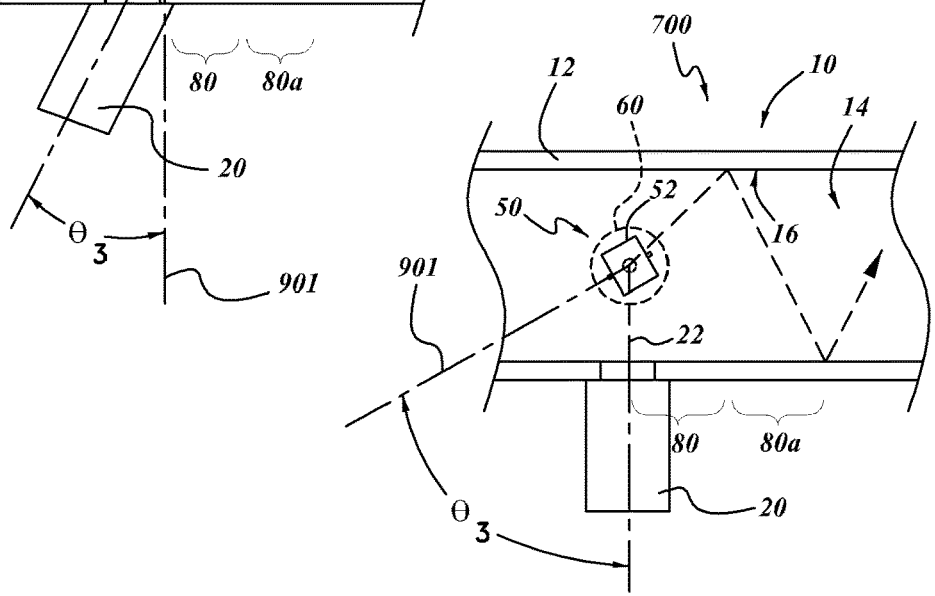

FIGS. 7A and 7B are top cross-sectional views of other embodiments of an air sterilization apparatus 600 and 700, respectively. Apparatuses 600 and 700 can include the energy source 20 and beam redirector 50, and many other similar components as apparatus 100 shown in FIGS. 2-3D. Apparatuses 600 and 700 can be configured such that beam 22 from energy source 20 and the axis of rotation 901 of optical element 52 are substantially non-collinear. Such positioning can form an angle $\theta_3$ between beam 22 and axis 901 that is greater than zero degrees, and less than 90 degrees. Such embodiments can allow beam 22 to reflect off surface 56 of optical element 52, and travel longitudinally down inner volume 14, to form energy field 80, and in some embodiments, form one or more reflected energy fields 80A, etc. The angle $\theta_3$ between beam 22 and axis 901 can be varied, for example, by positioning energy source 20 (and thus beam 22) at a substantially non-orthogonal angle relative to sidewalls 12 (FIG. 7A), or positioning beam redirector 50 such that axis 901 is at a non-orthogonal angle relative to sidewalls 12.

In some embodiments, one or more objects other than air can be placed within the chambers of the air sterilization apparatuses described herein. Such embodiments can allow for one or more objects such as medical tools and the like, placed within the chambers of the apparatus to be sterilized.

Figure 8A:
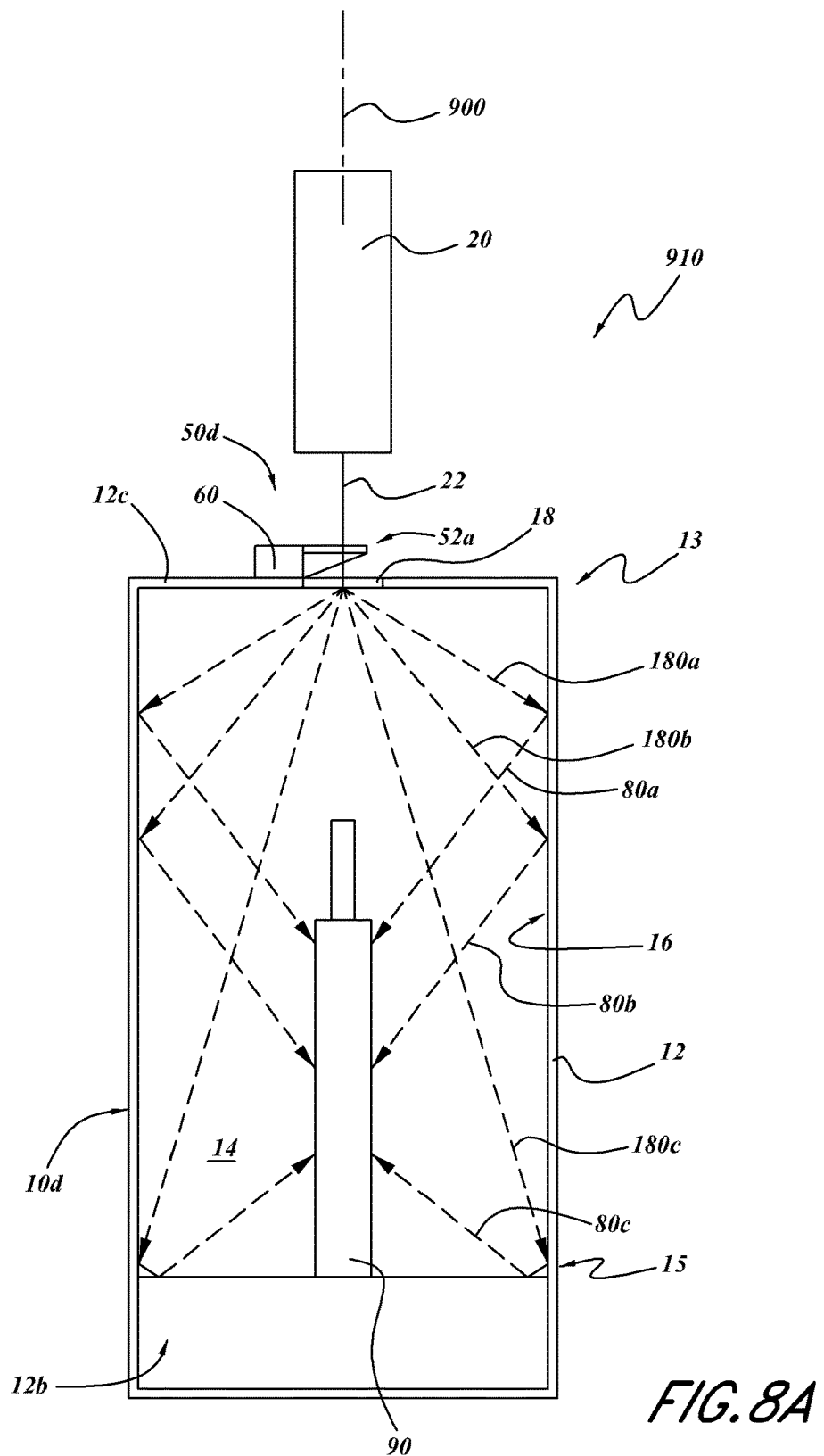
FIG. 8A is a side cross-sectional view of an embodiment of an air sterilization apparatus configured to sterilize objects within a chamber.

FIG. 8A is a side cross-sectional view of an embodiment of an air sterilization apparatus 910 configured to sterilize one or more objects within a chamber 10D. Chamber 10D can include a base 12B and a cover 12C to cover ends 15, 13, respectively, of chamber 10D. As such, chamber 10D can form a substantially enclosed interior volume 14. A rotating beam redirector 50D can be configured to direct beam 22 through opening 18 and form a plurality of energy fields 180A-180C, which can reflect off surface 16, and form reflected fields 80A-80C, which can impact and thus sterilize a tool 90 positioned on base 12B. Additionally, the thermal energy from surfaces directly impacted by the energy fields can flow via conduction over non-directly energy impacted surfaces, to further achieve sterilization. In some embodiments, the optical element 52A can be configured to rotate in the X-plane, and/or oscillate around axis 900, to provide the energy fields and reflected fields shown. In some embodiments, the optical element 52A can be configured to move in the Y-plane while the aforementioned X-plane rotation/oscillation is ongoing.

FIG. 8B is a side cross-sectional view of another embodiment of an air sterilization apparatus 1000 configured to sterilize one or more objects within a chamber 10E. Chamber 10E can be a substantially enclosed chamber, as shown in FIG. 8A. In this embodiment, a rotating beam redirector 50E can be configured to direct beam 22 through opening 18, and form a plurality of energy fields 280A-280C, which can reflect off surface 16, and form reflected fields 80A-80E, which can impact and thus sterilize the tool 90 positioned on the base 12B. In some embodiments, one or more chambers can be rotated through energy fields, so that the entirety of the outer surface of the tool is impacted with energy and sterilized.

FIG. 8C is a side cross-sectional view of an embodiment of an air sterilization apparatus 1100 that includes a plurality of the sterilization chambers 10E shown in FIG. 8B. Air sterilization apparatus 1100 can include a plurality of stations in a conveyor, carousel or other suitable movable multi-platform manufacturing configuration, to allow a plurality of tools 90 in a plurality of sterilization chambers 10E, to be sterilized consecutively by air sterilization apparatus 1000.

Figure 9:
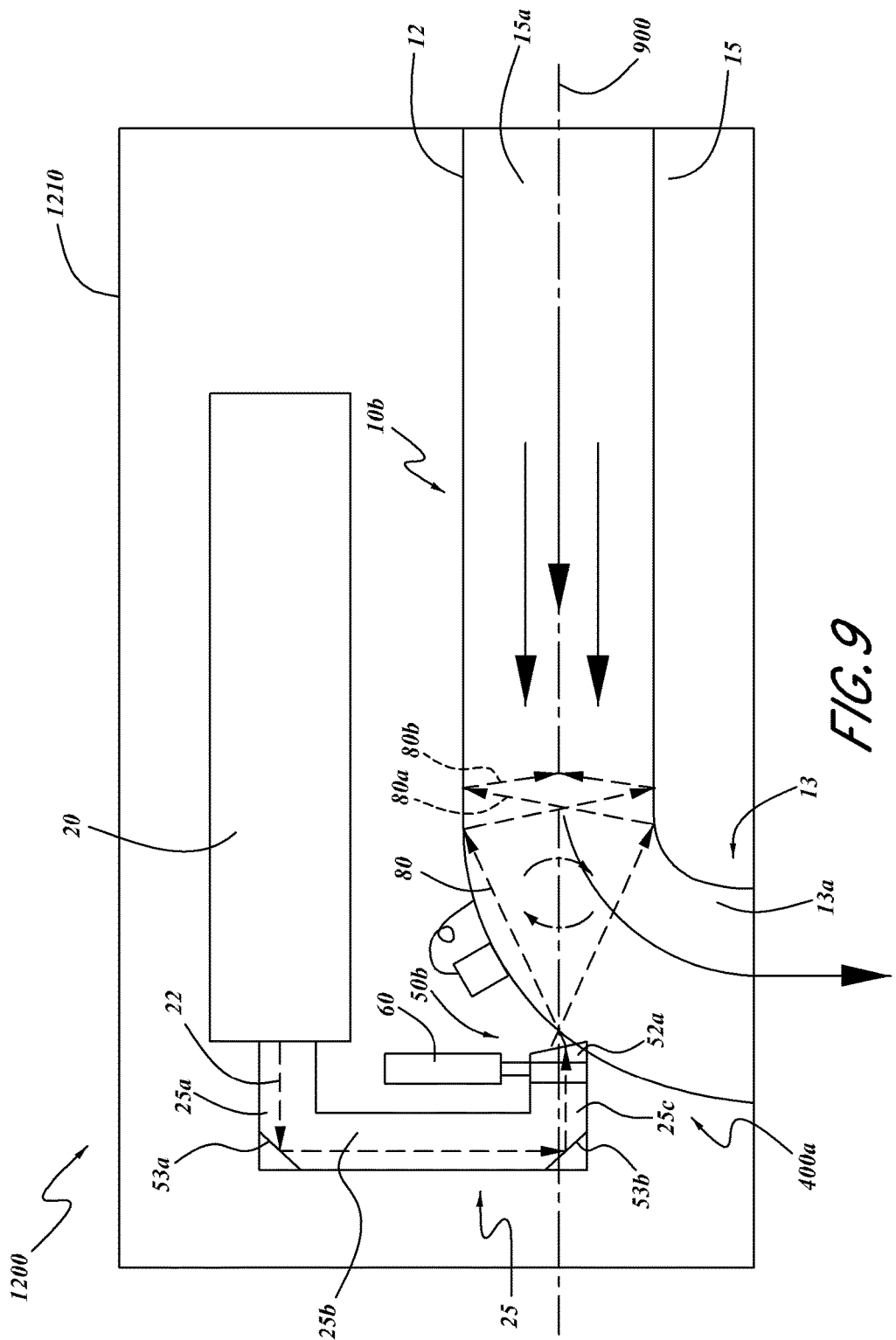
FIG. 9 is a side schematic view of another embodiment of an air sterilization apparatus.

FIG. 9 is a side schematic view of another embodiment of an air sterilization apparatus 1200. Apparatus 1200 can include an outer housing 1210, which can support and enclose an air sterilization system 400A that is similar to system 400 shown in FIGS. 5A-5B. A difference is that apparatus 1200 can include the inner channel 25 to route energy beam 22 from energy source 20 to the optical element 52A of beam redirector 50B. One or more reflective elements can be positioned within inner channel 25, to direct energy beam 22 therethrough. For example, the energy beam 22 can be directed (e.g., horizontally) through a first (e.g. horizontal) section 25A of channel 25, and change direction (e.g., vertically) after reflecting off a first reflective element 53A. Beam 22 can then be directed (e.g., vertically) through a second (e.g., vertical) section 25B of channel 25, and change direction (e.g., horizontally) after reflecting off a second reflective element 53B. Beam 22 can then be directed (e.g., horizontally) through a third (e.g., horizontal) section 25C of channel 25, to optic element 52A. In this way, beam 22 can be directed into beam redirector 50B in an orientation approximately opposite to the direction of beam 22 from energy source 20. Beam 22 can then pass through optic element 52A, which can be rotated to form energy field 80, similar to apparatus 400 (FIGS. 5A-5B). By including reflective elements 53A and 53B, and allowing for the redirection of energy beam 22 prior to it being further redirected by beam redirector 50B, energy source 20 can be oriented in a way that can reduce the overall space envelope of apparatus 1200. Such embodiments can allow for a compact, portable air sterilization apparatus that can be employed within confined spaces, such as windows, doors, walls, or other openings within, for example, a dwelling or vehicle, such as an aircraft. It will be understood that one or more reflective elements similar to elements 53A and 53B in FIG. 9, can be employed with any of the embodiments described herein, to allow for various positionings of energy source 20 and to orient the reflective beam 22 from the energy source 20 in different ways.

Some embodiments of the present application relate to a method of purifying or sterilizing air. In an embodiment, the air purification method comprises flowing air into an interior volume of a chamber; directing a beam of collimated light energy into the chamber; and imparting a charge to one or more walls of the chamber to repel particles within the interior volume from one or more sidewalls of the chamber. Some embodiments further include reflecting the beam of collimated light energy off at least one sidewall. Imparting a charge can include imparting a negative charge. Some embodiments further include imparting a similar charge to particles within the interior volume of the chamber.

In another embodiment, the air purification method comprises directing a beam of collimated light energy into an interior volume of a chamber; rotating the beam of collimated light energy within the interior volume about a rotational axis; and redirecting the beam of collimated light energy to form a field of collimated light energy extending across substantially an entirety of a cross sectional area of the interior volume and extending longitudinally along a longitudinal axis within the interior volume. Some embodiments further comprise flowing air through an opening into the interior volume, and from the interior volume through a second opening. Some embodiments further comprise reflecting the field of collimated light energy to form a reflected field of collimated light energy extending across substantially an entirety of a cross sectional area of the interior volume and extending longitudinally along a longitudinal axis within the interior volume.

In another embodiment, the air purification method comprises directing a beam of collimated light energy of width W into an interior volume of a chamber; and rotating the beam of collimated light energy within the interior volume about a rotational axis at a rotational velocity corresponding to at least V/W, wherein V is the linear velocity of a particle within the chamber along the longitudinal axis. Some embodiments further comprise adjusting the linear velocity of the particle within the chamber by adjusting the amount of airflow through the chamber. In some embodiments, rotating comprises rotating the beam of collimated light energy a complete revolution about a rotational axis such that the beam of collimated light energy is redirected to form a field of collimated light energy extending across substantially an entirety of a cross sectional area of the interior volume during said revolution. In some embodiments, rotating further comprises extending the field of collimated light energy longitudinally along the longitudinal axis. Some embodiments further comprise adjusting the wavelength of the beam of collimated light energy As described above, the speed of the rotation of the rotating optical element within embodiments of the air sterilization apparatus described herein may be adjusted via any method known to those having skill in the art, including adjustment via the controller. The below examples illustrate that the speed of the rotation of the optical element can be configured so that the energy field impacts approximately 100% of any particles traveling in the airstream.

Example 1: Cylindrical Ventilation Duct

This example discusses how the field of laser energy impacts an increased portion, such as up to approximately 100% of the particulates in a ventilation airstream traveling through a cylindrical ventilation duct, such as the embodiment shown with respect to FIGS. 4A-6B.

Those having skill in the art recognize that ventilation systems are generally constructed to contain a laminar air flow. Laminar air flow requires a Reynolds Number ($N_R$) that is less than 3,000. An $N_R$ above 3,000 will result in turbulent flow. Note: the change from laminar to turbulent flow can be reached at $N_R$=2,000 and as low as $N_R$=1,000.

For this example, we will select the highest $N_R$ that still describes a laminar flow: 3,000. We select the worst case scenario parameters for the example to demonstrate functionality in the extreme and thus also the norm.

The Reynolds Number ($N_R$) is given by:

$$N_R = \frac{d\rho N}{n} => V = \frac{N_R n}{d\rho}$$

Where: d=diameter of vent (meters)
$\rho$=density of air $$\left(\frac{kg}{m^3}\right)$$

V=linear air flow rate within vent $$\left(\frac{meters}{second}\right)$$

n=viscosity of air (pascals×second)
For example purposes, the following assumption will be made:
The temperature of air within the vent is T=20° C.=68° F.
By definition, at 20° C. the density of air is $$\rho = 1.204 \frac{kg}{m^3}$$

and the viscosity of air is n=0.018 m Pas=0.018×10$^{-3}$ Pas=0.000018 Pas.

As we determined earlier the linear air flow rate is given by:

$$V = \frac{N_R n}{d\rho}$$

Therefore, for $N_R$=3,000

$$V_{3,000} = \frac{3000 \times 0.018 \times 10^{-3} \text{ Pas}}{0.2032 \text{ m} \times 1.204 \text{ kg/m}^3} = \frac{0.054 \frac{kg \times s}{s^2 \times m}}{0.2447 \frac{kg}{m^2}} = 0.221 \frac{m}{s} \times \frac{1 \text{ ft}}{0.3048 \text{ m}}$$

Thus, the maximum possible laminar air flow rate within the vent yields a particle linear speed of:

$V_{3,000}$=0.724 ft/sec=0.221 m/s

Our example will continue by setting a revolution per minute (RPM) for the refractive window that is equivalent to the time it takes a dimensionless particle (so used to negate a limitation of the system by nanometer sized particles) to travel a distance equivalent to the width of the laser beam. This will ensure that each particulate is impacted by the laser at least once, in a single rotation of the optical element, which forms a single energy field. In addition, reflections of the energy field down the reflective vent will generate further impacts for any remaining particles not completely destroyed by a single impact with the laser beam.

For this example, a laser beam of width 2 mm will be used.

The time that it takes a particulate to travel the width of this laser beam is:

$$T = \frac{D}{V} = \frac{2 \text{ mm}}{0.724 \text{ ft/sec}} = \frac{2 \times 10^{-3} \text{ m}}{0.221 \text{ m/sec}} = 0.00905 \text{ sec}$$

Now, from the time that the particulate travels the width of the beam, the optical element must rotate the beam once around the circumference of the vent. Doing so will increase the likelihood of any particulate passing through the "laser field" without being hit by the laser beam; as mentioned above. The optical element must therefore rotate at a velocity (v) of:

$$v = \frac{D}{T} = \frac{\text{circumference}}{0.00905 \text{ sec}} = \frac{2\pi r}{0.00905 \text{ sec}} = \frac{0.6387 \text{ m}}{0.00905 \text{ sec}} = 70.57 \frac{\text{m}}{\text{s}}$$

Continuing unit's yields:

v=70.57 meter/sec×rev/0.6387 meter×60 sec/min=6,629 rev/min (rpm)

Thus, for the maximum airflow that will be found in any laminar ventilation system, the field of laser energy created using a 2 mm beam in an 8 inch diameter ventilation duct with a refractive window that is rotating at 7,000 rpm will impact approximately 100% of particulate.

Following this same example, a 1 mm beam in an 8 inch diameter chamber rotated at approximately 12,600 rpm will impact approximately 100% of particulate.

Also, following this example a chamber with a 6 ft diameter and a 1 mm beam will yield
$V_{3000}$=0.0245 m/s
T=0.04078 seconds
V=140.886 m/s=>V=1,471.31 rpm Example 2: Square Ventilation Duct This example discusses how the field of laser energy achieves an increased impact of approximately 100% of particulate in a ventilation airstream, for example, in a square chamber, such as that shown in FIGS. 2-3D. Additional test results provided elsewhere herein describe how enough energy can be imparted through each laser/particle impact to kill each biological molecule impacted.

Those familiar with the art recognize that ventilation systems are constructed to contain a laminar air flow. Laminar air flow requires a Reynolds Number ($N_R$) that is less than 3,000. An $N_R$ above 3,000 will result in turbulent flow. Note: the change from laminar to turbulent flow can be reached at $N_R$=2,000 and as low as $N_R$=1,000.

For this example, we will select the highest $N_R$ that still describes a laminar flow: 3,000. We select the worst case scenario parameters for the example to demonstrate functionality in the extreme and thus also the norm.

The Reynolds Number ($N_R$) for a square duct is given by:

$$N_R = \frac{\rho V D_H}{n} = \frac{\rho V L}{n} => V = \frac{N_R n}{L\rho}$$

Where: v=linear mean velocity (meters/seconds)

$$\rho = \text{density of air}\left(\frac{\text{kg}}{\text{m}^3}\right)$$

n=viscosity of air (pascals×second)

$D_H$=Hydraulic diameter=L=length of square vent

For example purposes, the following assumption will be made:

The temperature of air within the vent is T=20° C.=68° F.

By definition, at 20° C. the density of air is $$\rho = 1.204\frac{\text{kg}}{\text{m}^3}$$

and the viscosity of air is n=0.018 m Pas=0.018×$10^{-3}$ Pas=0.000018 Pas.

As we determined earlier the linear air flow rate is given by:

$$V = \frac{N_R n}{L\rho}$$

Therefore, for $N_R$=3,000

$$V_{3,000} = \frac{3000\times 0.018\times 10^{-3}\text{ Pas}}{0.3048\text{ m}\times 1.204\text{ kg/m}^3} = \frac{0.054\frac{\text{kg}\times\text{s}}{\text{s}^2\times\text{m}}}{0.36698\frac{\text{kg}}{\text{m}^2}} = 0.147\frac{\text{m}}{\text{s}}\times\frac{1\text{ ft}}{0.3048\text{ m}} = 0.483\frac{\text{ft}}{\text{s}}$$

Thus, the maximum possible laminar air flow rate within the vent yields a particle linear speed of:

$V_{3,000}$=0.483 ft/sec=0.147 m/sec

Our example will continue by setting a revolution per minute (RPM) for the reflective plate that is equivalent to the time it takes a dimensionless particle (used to negate a limitation of the system by nanometer sized particles) to travel a distance equivalent to the width of the laser beam. This will ensure that each particulate is hit by the laser at least once. There will be a vortex created by the plate. However, the 1st reflection off the reflective surface of the ventilation duct will fill that vortex space with energy thereby sterilizing it.

For this example, a laser beam of width 3 mm will be used.

The time that it takes a particulate to travel the width of this laser beam is:

$$T = \frac{D}{V} = \frac{3 \text{ mm}}{0.247 \text{ m/sec}} = \frac{3 \times 10^{-3} \text{ m}}{0.147 \text{ m/sec}} = 0.0204 \text{ sec}$$

Now, from the time that the particulate travels the width of the beam, the reflective plate must rotate the beam once around the circumference of the vent. Doing so will guarantee that no particulate will pass through the "laser field" without being hit by the laser beam; as mentioned above. The refractive window must therefore rotate at a velocity (v) of:

$$v = \frac{D}{T} = \frac{\text{perimeter}}{0.0204\ \text{sec}} = \frac{4\ \text{L}}{0.0204\ \text{sec}} = \frac{4 \times 0.3048\ \text{m}}{0.0204\ \text{sec}} = 59.75\ \text{m/s}$$

Continuing unit's yields:

$$v = 59.75\ \text{meter/sec} \times \text{revolution}/1.2192\ \text{meter} \times 60\ \text{sec/min} \Rightarrow 2{,}940.5\ \text{rev/min (rpm)}$$

Thus, for the maximum airflow that will be found in any square laminar ventilation system, the field of laser energy created using a 3 mm beam in a 1 ft×1 ft square diameter ventilation duct with a reflective plate that is rotating at 3,000 rpm will impact approximately 100% of particulate.

Examples 1 and 2 above can be similarly employed for other cylindrical or square shaped chambers, or chambers of other shapes, to increase the likelihood of particulate traveling at a given velocity to be impacted by an energy beam in a single rotation of the optical element. It will be understood that although Examples 1 and 2 employ laminar flow examples, higher linear speed velocities creating turbulent flows (such as in laboratory exhaust plumes) can be similarly purified and/or sterilized through similar use of beam width, beam director rotational velocity, and linear velocity of a particle within a ventilation system air stream.

All references cited herein are incorporated herein by reference in their entirety. To the extent publications and patents or patent applications incorporated by reference contradict the disclosure contained in the specification, the specification is intended to supersede and/or take precedence over any such contradictory material.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only.

What is claimed is:

1. An air purification apparatus, comprising:

a chamber comprising a first end with a first opening, and a second end with a second opening, and one or more substantially continuous walls extending substantially continuously between the first opening and the second opening to form an interior volume, wherein at least one of the walls comprises a reflective surface facing inwardly towards the interior volume;

a collimated light source configured to direct a beam of collimated light energy into the chamber; and a charge generation system configured to impart a charge to the one or more substantially continuous walls, to repel particles contained within the interior volume from the one or more walls.

2. The air purification apparatus of claim 1, wherein the charge generation system is configured to impart a similar charge on the particles within the interior volume.

3. The air purification apparatus of claim 1, wherein the charge generation system is configured to impart a negative charge.

4. The air purification apparatus of claim 1, wherein the collimated light source is a laser.

5. The air purification apparatus of claim 1, wherein the chamber is cylindrical.

6. The air purification apparatus of claim 1, further comprising a beam redirector disposed within the interior volume and configured to rotate through a complete revolution about a rotational axis such that the beam of collimated light energy is redirected within the chamber during said revolution.

7. The air purification apparatus of claim 6, wherein the beam redirector is configured to redirect the beam of collimated light energy to form a field of collimated light energy extending across substantially an entirety of a cross sectional area of the interior volume and longitudinally within the interior volume.

8. The air purification apparatus of claim 7, further comprising an energy abatement device positioned within the chamber and configured to absorb the energy of the field of collimated light energy.

9. The air purification apparatus of claim 6, further comprising a controller configured to rotate the beam redirector about the rotational axis at a rotational velocity corresponding to V/W, wherein V is the linear velocity of a particle within the chamber along the longitudinal axis, and W is the width of the beam of collimated light energy.

10. The air purification apparatus of claim 1, wherein the chamber comprises a first end and a second end configured to allow air to flow through the interior volume from the first end to the second end along a longitudinal axis.

11. An air purification apparatus comprising:

a chamber comprising:
- one or more sidewalls forming an interior volume, the one or more sidewalls comprising one or more surfaces facing inwardly towards the interior volume; and
- a first opening and a second opening configured to allow air to flow through the interior volume from the first opening to the second opening along a longitudinal axis;

a collimated light source configured to direct a beam of collimated light energy into the interior volume of the chamber;

a beam redirector disposed within the interior volume and configured to rotate through a complete revolution about a rotational axis such that the beam of collimated light energy is redirected to form a field of collimated light energy extending across substantially an entirety of a cross sectional area of the interior volume during said revolution; and a controller configured to rotate the beam redirector about the rotational axis at a rotational velocity corresponding to at least V/W, wherein V is the linear velocity of a particle within the chamber along the longitudinal axis, and W is the width of the beam of collimated light energy.

12. The air purification apparatus of claim 11, wherein the field of collimated light energy comprises a plurality of coplanar reflected beams.

13. The air purification apparatus of claim 11, wherein the field of collimated light energy extends longitudinally along the longitudinal axis.

14. The air purification apparatus of claim 11, wherein the collimated light source is a laser.

15. The air purification apparatus of claim 11, wherein the chamber is cylindrical.

16. The air purification apparatus of claim 11, wherein the controller is configured to adjust the wavelength of the beam of collimated light energy.

17. The air purification apparatus of claim 11, wherein the controller is configured to adjust the amount of air flowing through the chamber.

18. The air purification apparatus of claim 11, further comprising a charge generation system configured to impart a charge to the one or more walls, to repel similarly charged particles contained within the interior volume from the one or more walls.

19. The air purification apparatus of claim 18, wherein the controller is configured to adjust the amount of charge imparted to the one or more walls.

* * * * *